United States Patent
Avidor et al.

(10) Patent No.: US 9,839,396 B2
(45) Date of Patent: Dec. 12, 2017

(54) METHOD AND SYSTEM FOR ASSESSING LIKELIHOOD OF SEPSIS

(71) Applicant: Cheetah Medical, Inc., Wilmington, DE (US)

(72) Inventors: Yoav Avidor, Tel-Aviv (IL); Baruch Levy, LeHavim (IL)

(73) Assignee: Cheetah Medical, Inc., Wilmington, DE (US)

( * ) Notice: Subject to any disclaimer, the term of this patent is extended or adjusted under 35 U.S.C. 154(b) by 369 days.

(21) Appl. No.: 14/405,495

(22) PCT Filed: Jun. 5, 2013

(86) PCT No.: PCT/IB2013/054615
§ 371 (c)(1),
(2) Date: Dec. 4, 2014

(87) PCT Pub. No.: WO2013/183001
PCT Pub. Date: Dec. 12, 2013

(65) Prior Publication Data
US 2015/0148695 A1    May 28, 2015

Related U.S. Application Data

(60) Provisional application No. 61/655,571, filed on Jun. 5, 2012.

(51) Int. Cl.
*A61B 5/053* (2006.01)
*A61B 5/0265* (2006.01)
(Continued)

(52) U.S. Cl.
CPC ............ *A61B 5/7275* (2013.01); *A61B 5/029* (2013.01); *A61B 5/0265* (2013.01);
(Continued)

(58) Field of Classification Search
CPC ..... A61B 5/7275; A61B 5/0265; A61B 5/029; A61B 5/0488; A61B 5/053; A61B 5/11; A61B 5/412; A61B 5/7278
(Continued)

(56) References Cited

U.S. PATENT DOCUMENTS 7,529,579 B2 * 5/2009 Colombo .......... A61B 5/02405
                                                    600/513
7,941,199 B2    5/2011 Kiani
(Continued)

FOREIGN PATENT DOCUMENTS

CN    1665940    9/2005
CN    102472756  5/2012
(Continued)

OTHER PUBLICATIONS

Notification of Office Action dated Aug. 10, 2016 From the State Intellectual Property Office of the People's Republic of China Re. Application No. 201380029446.0 and Its Translation Into English.
(Continued)

*Primary Examiner* — Navin Natnithithadha (57) ABSTRACT

A method of assessing the likelihood that an infected subject develops sepsis, using an input radiofrequency signal received from the subject responsively to an output radiofrequency signal transmitted to the subject. The method comprises: processing the input signal to provide a processed signal, analyzing the processed signal to determine a characteristic pulse morphology of the processed signal, and using the characteristic pulse morphology for assessing the likelihood that the subject develops sepsis.

20 Claims, 7 Drawing Sheets

(51) Int. Cl.
*A61B 5/029* (2006.01)
*A61B 5/0488* (2006.01)
*A61B 5/11* (2006.01)
*A61B 5/00* (2006.01)

(52) U.S. Cl.
CPC ............ *A61B 5/0488* (2013.01); *A61B 5/053* (2013.01); *A61B 5/11* (2013.01); *A61B 5/412* (2013.01); *A61B 5/7278* (2013.01)

(58) Field of Classification Search
USPC ....... 600/481, 483, 484, 500–504, 513, 509, 600/508
See application file for complete search history.

(56) References Cited

U.S. PATENT DOCUMENTS

| | | | | |
|---|---|---|---|---|
| 7,949,389 | B2* | 5/2011 | Wolfberg | A61B 5/4362 600/376 |
| 8,029,982 | B2 | 10/2011 | Kingsmore et al. | |
| 8,585,607 | B2* | 11/2013 | Klap | A61B 5/0205 600/534 |
| 8,615,291 | B2* | 12/2013 | Moorman | A61B 5/02405 600/509 |
| 8,734,360 | B2* | 5/2014 | Klap | A61B 5/0205 600/484 |
| 8,821,418 | B2* | 9/2014 | Meger | A61B 5/0002 600/595 |
| 8,892,181 | B2* | 11/2014 | Wolfberg | A61B 5/0444 600/391 |
| 9,380,947 | B2* | 7/2016 | Levy | A61B 5/029 |
| 2003/0194752 | A1 | 10/2003 | Anderson et al. | |
| 2006/0100534 | A1* | 5/2006 | Colombo | A61B 5/02405 600/513 |
| 2006/0246495 | A1 | 11/2006 | Garrett et al. | |
| 2009/0069647 | A1* | 3/2009 | McNames | A61B 5/0205 600/301 |
| 2009/0259133 | A1* | 10/2009 | Wolfberg | A61B 5/4362 600/511 |
| 2009/0281839 | A1* | 11/2009 | Lynn | G06F 19/321 705/3 |
| 2009/0287102 | A1* | 11/2009 | Ward | A61B 5/0265 600/506 |
| 2010/0234748 | A1* | 9/2010 | Moorman | A61B 5/02405 600/509 |
| 2011/0046498 | A1* | 2/2011 | Klap | A61B 5/0205 600/534 |
| 2011/0112442 | A1* | 5/2011 | Meger | A61B 5/0002 600/595 |
| 2011/0118569 | A1 | 5/2011 | Shi et al. | |
| 2011/0137852 | A1 | 6/2011 | Gajic et al. | |
| 2011/0178418 | A1 | 7/2011 | Avidor et al. | |
| 2012/0016209 | A1* | 1/2012 | Wolfberg | A61B 5/4362 600/301 |
| 2012/0083676 | A1* | 4/2012 | Wolfberg | A61B 5/4362 600/301 |
| 2013/0209068 | A1* | 8/2013 | Lynn | G06F 19/321 386/278 |
| 2014/0005502 | A1* | 1/2014 | Klap | A61B 5/113 600/301 |
| 2014/0046209 | A1* | 2/2014 | Klap | A61B 5/0205 600/534 |
| 2015/0366468 | A1* | 12/2015 | Levy | A61B 5/029 600/526 |
| 2016/0310013 | A1* | 10/2016 | Levy | A61B 5/029 |
| 2016/0310014 | A1* | 10/2016 | Levy | A61B 5/029 |
| 2016/0310015 | A1* | 10/2016 | Levy | A61B 5/029 |
| 2016/0310016 | A1* | 10/2016 | Levy | A61B 5/029 |

FOREIGN PATENT DOCUMENTS

| | | |
|---|---|---|
| WO | WO 2004/005539 | 1/2004 |
| WO | WO 2013/183001 | 12/2013 |

OTHER PUBLICATIONS

Notification of Office Action dated Dec. 13, 2016 From the State Intellectual Property Office of the People's Republic of China Re. Application No. 201380029446.0 and Its Translation Into English. (14 Pages).
International Preliminary Report on Patentability dated Dec. 18, 2014 From the International Bureau of WIPO Re. Application No. PCT/IB2013/054615.
International Search Report and the Written Opinion dated Oct. 8, 2013 From the International Searching Authority Re. Application No. PCT/IB2013/054615.
Notification of Office Action and Search Report dated Nov. 3, 2015 From the State Intellectual Property Office of the People's Republic of China Re. Application No. 201380029446.0.
Translation dated Nov. 17, 2015 of Notification of Office Action dated Nov. 3, 2015 From the State Intellectual Property Office of the People's Republic of China Re. Application No. 201380029446.0.
Notification of Office Action dated Jul. 31, 2017 From the State Intellectual Property Office of the People's Republic of China Re. Application No. 201380029446.0. (3 Pages).
Translation of Notification of Office Action dated Jul. 31, 2017 From the State Intellectual Property Office of the People's Republic of China Re. Application No. 201380029446.0. (2 pages).

* cited by examiner

METHOD AND SYSTEM FOR ASSESSING LIKELIHOOD OF SEPSIS

RELATED APPLICATIONS

This application is a National Phase of PCT Patent Application No. PCT/IB2013/054615 having International filing date of Jun. 5, 2013, which claims the benefit of priority under 35 USC §119(e) of U.S. Provisional Patent Application No. 61/655,571 filed Jun. 5, 2012. The contents of the above applications are all incorporated by reference as if fully set forth herein in their entirety.

FIELD AND BACKGROUND OF THE INVENTION

The present invention, in some embodiments thereof, relates to medical application and, more particularly, but not exclusively, to a method and system for assessing likelihood of sepsis.

Early detection of a disease condition typically allows for a more effective therapeutic treatment with a correspondingly more favorable clinical outcome. In many cases, however, early detection of disease symptoms is problematic due to the complexity of the disease; hence, a disease may become relatively advanced before diagnosis is possible. Sepsis represents one such class of diseases.

Sepsis is the name given to infection when symptoms of inflammatory response are present. Sepsis is defined as an infection-induced syndrome involving two or more of the following features of systemic inflammation: fever or hypothermia, leukocytosis or leukopenia, tachycardia, and tachypnea or a supranormal minute ventilation. Sepsis results either from community-acquired infections or hospital-acquired infections.

The cause of a sepsis can be infection of any origin, including bacterial, viral and parasitic origin, or it can be caused by fungi. This infection can occur anywhere in the body. The most common sites of infection in patients with sepsis are lung, gut, urinary tract, and primary blood stream site of infection. Since sepsis can be caused by many types of infection with microorganisms at many different sites, sepsis is a very heterogeneous disease.

Sepsis can affect anybody at any age, although young or very old hospital patients and persons with existing disease conditions have a higher risk. Risk factors include a too little active immune system (as can arise, for example, during a chemotherapy or is caused by medicine intended to permit an organ transplantation; by surgical procedures; artificial respiration; genetic predisposition or in invasive procedures, such as the supply of liquids).

Severe sepsis is defined as sepsis associated with acute organ dysfunction, wherein the risk of death from sepsis increases with increasing severity. Sepsis is the leading cause of death in critically ill patients, particularly among patients in non-coronary intensive care units.

The course of the sepsis can be described as a sequence of various processes. When the sepsis begins, the body reacts with expanded inflammations, blood clotting and impaired decomposition of blood clots.

Under normal circumstances, substances, also referred to as immunomodulators, are released in order to support the body in combating the infection during the healing process itself. With a person suffering from sepsis, this mechanism breaks down and the immunoregulators lead to an overshooting reaction. The infection enhances the release of too many of these regulators which inflame the lining of the blood vessels and the processes for blood coagulation are activated, this process triggering another wave releasing regulators.

The inflammation leads to the release of a substance stimulating the formation of blood clots. In the sepsis cascade, the body's ability to decompose the blood clots is suppressed. A substance involved in the formation of the blood clot, the control of the inflammation and the decomposition of clots, referred to as activated protein C, is reduced in a sepsis. As a result of the formation of blood clots and the inability to decompose these clots, microscopic blood clots start to deposit in vital organs, arms and legs and restrict the blood flow leading to tissue damages which can lead to organ failure.

Sepsis is typically diagnosed either by clinical criteria or by culture of microorganisms from the blood of patients suspected of having sepsis plus the presence of features of systemic inflammation. Bloodstream infection is diagnosed by identification of microorganisms in blood specimens from a patient suspected of having sepsis after 24 to 72 hours of laboratory culture. For each class of infection, there are several different types of microorganisms that can cause sepsis.

Techniques for early detection of sepsis are found in, e.g., U.S. Pat. Nos. 8,029,982 and 7,941,199, and in U.S. Published Application Nos. 20110118569, 20030194752 and 20060246495.

SUMMARY OF THE INVENTION

According to an aspect of some embodiments of the present invention there is provided a method of assessing the likelihood that an infected subject develops sepsis, using an input radiofrequency signal received from the subject responsively to an output radiofrequency signal transmitted to the subject. The method comprises: processing the input signal to provide a processed signal, analyzing the processed signal to determine a characteristic pulse morphology of the processed signal, and using the characteristic pulse morphology for assessing the likelihood that the subject develops sepsis.

According to an aspect of some embodiments of the present invention there is provided a method of assessing the likelihood that an infected subject develops sepsis. The method comprises: transmitting an output radiofrequency signal to the subject, receiving an input radiofrequency signal from the subject; and executing the method described above.

According to some embodiments of the invention the method further comprises using the processed signal for calculating a blood flow quantity, wherein the likelihood is assessed based, at least in part, on the blood flow quantity.

According to some embodiments of the invention the determination of the characteristic pulse morphology comprises extracting a time-derivative of the processed signal.

According to some embodiments of the invention the method comprises using the processed signal for calculating a ventricular ejection time, and extracting a time-derivative of the processed signal, wherein the determining the characteristic pulse morphology comprises calculating a ratio between the time-derivative and the ventricular ejection time.

According to some embodiments of the invention the assessment of likelihood comprises comparing the ratio to a predetermined threshold, wherein a ratio above the predetermined threshold indicates that the subject is likely to develop sepsis.

According to some embodiments of the invention the processing comprises acquiring an absolute component and a phase component of the input signal, wherein the analyzing the processed signal comprises separately analyzing at least one of the phase component and the absolute component.

According to some embodiments of the invention the invention the method comprises identifying disturbances in the input signal based on the absolute component, and correcting the characteristic pulse morphology according to the identified disturbances.

According to some embodiments of the invention the method comprises identifying body movements of the subject based on the absolute component.

According to some embodiments of the invention the method comprises identifying muscle activity of the subject based on the absolute component.

According to an aspect of some embodiments of the present invention there is provided a computer software product. The product comprises a computer-readable medium in which program instructions are stored, which instructions, when read by a data processor, cause the data processor to receive a processed signal, to analyze the processed signal so as to determine a characteristic pulse morphology of the processed signal, and to calculate the likelihood that the subject develops sepsis based at least in part on the characteristic pulse morphology.

According to an aspect of some embodiments of the present invention there is provided a system for assessing the likelihood that an infected subject develops sepsis, using an input radiofrequency signal received from the subject responsively to an output radiofrequency signal transmitted to the subject. The system comprises: a signal processor configured for processing the input signal to provide a processed signal, an analyzer configured for analyzing the processed signal to determine a characteristic pulse morphology of the processed signal, and a likelihood calculator configured for calculating the likelihood that the subject develops sepsis based on the characteristic pulse morphology.

According to an aspect of some embodiments of the present invention there is provided a system for assessing the likelihood that an infected subject develops sepsis.

The system comprises a radiofrequency generator for generating an output radiofrequency signal; a plurality of electrodes designed for transmitting the output radiofrequency signal to the subject and for sensing an input radiofrequency signal from the subject; and the system described above.

According to some embodiments of the invention the system comprises a blood flow calculator configured for calculating blood flow using the processed signal, wherein the likelihood calculator is configured to calculate the likelihood based, at least in part, on the blood flow.

According to some embodiments of the invention the analyzer is configured for extracting a time-derivative of the processed signal.

According to some embodiments of the invention the analyzer is configured for calculating a ventricular ejection time using the processed signal, for extracting a time-derivative of the processed signal, and for calculating a ratio between the time-derivative and the ventricular ejection time.

According to some embodiments of the invention the likelihood calculator is configured to compare the ratio to a predetermined threshold, wherein a ratio above the predetermined threshold indicates that the subject is likely to develop sepsis.

According to some embodiments of the invention the threshold is from about 0.5 to about 0.8, and wherein the likelihood is characterized by a p-value less than 0.1.

According to some embodiments of the invention the signal processor comprises a signal separating unit configured for separating the input signal to an absolute component and a phase component, and wherein the analyzer is configured for separately analyzing at least one of the phase component and the absolute component.

According to some embodiments of the invention the analyzer is configured for identifying disturbances in the input signal based on the absolute component, and correcting the characteristic pulse morphology according to the identified disturbances.

According to some embodiments of the invention the analyzer is configured for identifying body movements of the subject based on the absolute component.

According to some embodiments of the invention the analyzer is configured for identifying muscle activity of the subject based on the absolute component.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to medical application and, more particularly, but not exclusively, to a method and system for assessing likelihood of sepsis.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Computer programs implementing the method according to embodiments of the present invention can commonly be distributed to users on a distribution medium such as, but not limited to, a floppy disk, CD-ROM and flash memory cards. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method, system and computer software product of the present embodiments are useful for assessing the likelihood that an infected subject develops sepsis. The assessment can include an assessment pertaining to the susceptibility of the subject to sepsis (for example, a prediction that the subject is likely to develop sepsis in the future). The assessment can also include an assessment that the subject is already septic.

The assessment can be provided in a binary manner, or in any other discrete or continuous manner. For example, when the assessment is defined in a binary manner (i.e., there are only two different likelihood levels) the likelihood that the subject develops sepsis can be "low" and "high" wherein "low" means that it is not likely that the subject develops sepsis, and "high" means that it is likely that the subject develops sepsis. As will be appreciated by one ordinarily skilled in the art, "low" and "high" can be represented numerically by, e.g., "0" and "1", respectively. Alternatively, more than two different likelihood levels can be defined and be assigned with a discrete or numerical value. A numerical value of the likelihood can be, for example, a statistical measure, such as a statistical significance, which can be expressed in terms of a p-value, as known in the art.

It was found by the present inventors that the likelihood that a subject develops sepsis can be assessed by determining a characteristic pulse morphology of a signal indicative of the impedance of an organ of the subject. The organ is preferably the thorax of the subject, but other organs such as, but not limited to, hip, thigh, neck, head, arm, forearm, abdomen, gluteus, leg and foot, are not excluded from the scope of the present invention.

Figure 1:
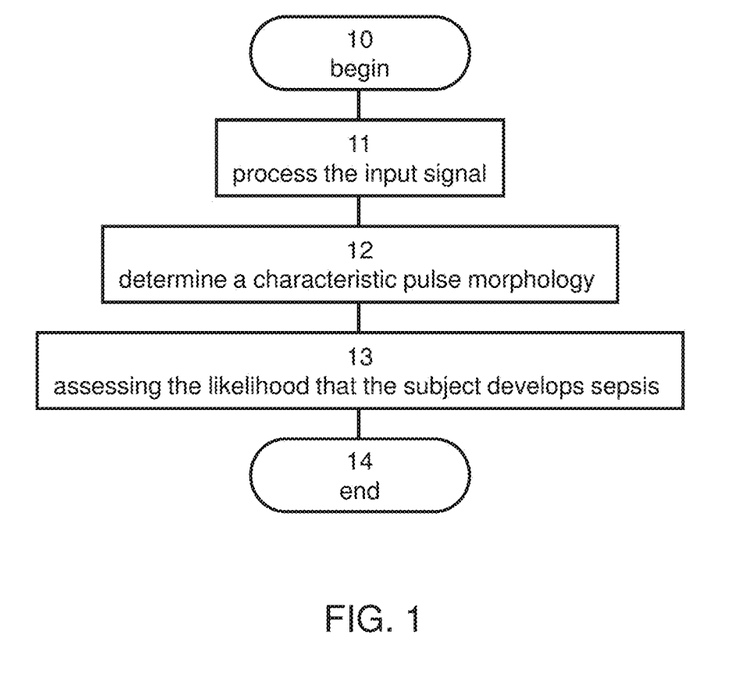
FIG. 1 is a flowchart diagram of a method suitable for assessing the likelihood that an infected subject develops sepsis, according to some embodiments of the present invention.

Referring now to the drawings, FIG. 1 is a flowchart diagram of a method suitable for assessing the likelihood that an infected subject develops sepsis, according to various exemplary embodiments of the present invention.

It is to be understood that, unless otherwise defined, the method steps described hereinbelow can be executed either contemporaneously or sequentially in many combinations or orders of execution. Specifically, the ordering of the flowcharts diagrams is not to be considered as limiting. For example, two or more method steps, appearing in the following description or in the flowchart diagrams in a particular order, can be executed in a different order (e.g., a reverse order) or substantially contemporaneously. Additionally, several method steps described below are optional and may not be executed.

The method is particularly useful for assessing the likelihood using an input radiofrequency signal received from the subject responsively to an output radiofrequency signal transmitted to the subject, wherein the input radiofrequency signal is indicative of the impedance of an organ of the subject.

The method begins at 10, and continues to 11, at which the input signal is processed, and 12 at which the processed signal is analyzed to determine a characteristic pulse morphology of the processed signal. The method continues to 13 at which the characteristic pulse morphology is used for assessing the likelihood that the subject develops sepsis.

The method ends at 14.

Figure 2:
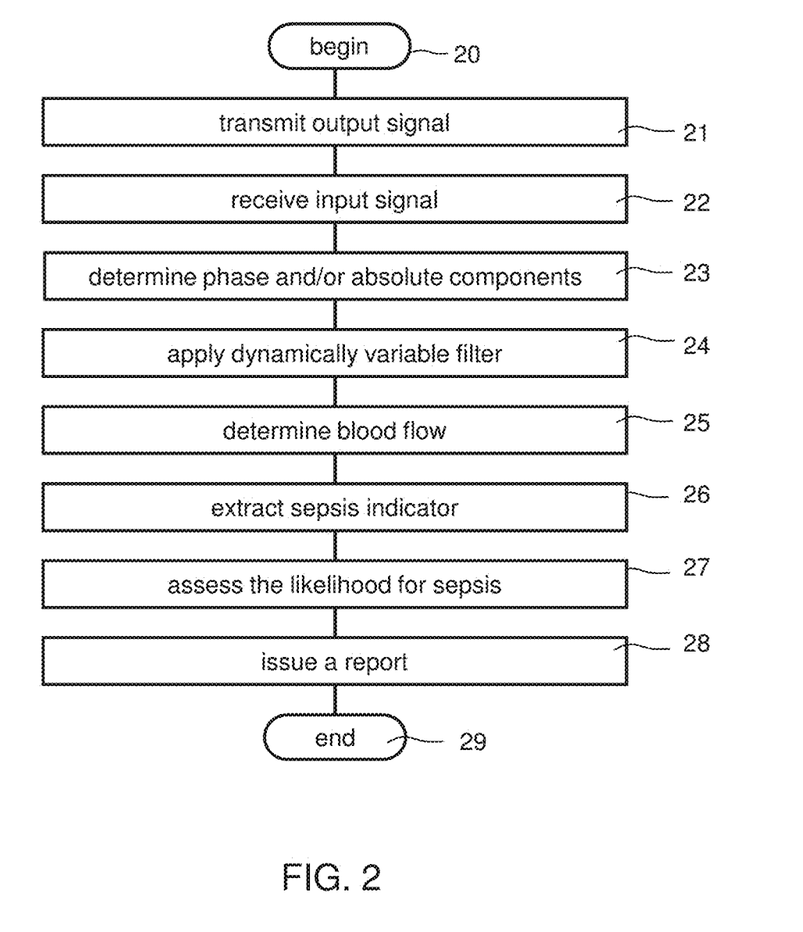
FIG. 2 is a flowchart diagram of a more detailed method suitable for assessing the likelihood that an infected subject develops sepsis, according to some embodiments of the present invention.

A more detailed method for monitoring sepsis according to some embodiments of the present invention is illustrated in the flowchart diagram of FIG. 2.

The method begins at 20 and optionally continues to 21 at which an output signal is transmitted to the subject, and 24 at which an input signal is received from the subject in response to the output signal. The output signals can be generated, for example, by a radiofrequency generator which generates a periodic high frequency current output in response to a periodic control input signal. The current output can be transmitted to the subject via an arrangement of electrodes for carrying current output from the radiofrequency generator as known in the art. The electrodes can be connected to locations of the body of the subject, e.g., above and below the heart.

Current, generated by the radiofrequency generator, flows across the thorax and causes a voltage drop due to the impedance of the body. The input radiofrequency signals are typically, but not obligatorily, relate to the impedance of an organ of the subject, or a component of the impedance, e.g., the reactance.

As used herein, "reactance" refers to the imaginary part of the impedance. Techniques for extracting the imaginary part from the total impedance are known in the art. Typically, such extraction is performed at hardware level but the use of algorithm at a software level is not excluded from the scope of the present invention.

The method optionally and preferably continues to 23 at which a phase component and/or an absolute component are extracted from the signal. The absolute and phase components can be acquired separately, namely via different circuitry channels which separate an input signal to an absolute component and a phase component. This allows the method to process each of these components independently, if desired.

At any given instance, any electrical signal can be described mathematically as a complex number.

As used herein, the term "absolute component" refers to the absolute value of this complex number, namely the length of the vector which describes the complex number in the complex plane, and the term "phase component" refers to the angle between the vector and the real axis in the complex plane.

Formally, denoting the complex number as A+jB, where A and B represent real numbers and j is a pure imaginary number satisfying $j^2=-1$, the absolute component of the input signal is given by $\sqrt{A^2+B^2}$, and the phase component is given by arctan (B/A).

In various exemplary embodiments of the invention the separation of the input signal into the absolute and phase components is by an analog processing unit. For example, the absolute component can be separated from the input signal by an envelope identifier which can be embodied as a circuit. The phase component can be separated from input signal by a mixer circuit configured for mixing the input signal with a signal indicative of a radiofrequency signal transmitted to the subject and filtering out a portion of mixed signal. A more detailed technique for separating the input signal to its components according to some embodiments of the present invention is described hereinunder.

It was found by the present inventors that a different type of information can be obtained from the phase component and the absolute component for any quantity that is directly or indirectly related to the blood flow. More specifically, in experiments performed by the present inventors, it was found that, unless the positive end expiratory pressure (PEEP) is artificially and abruptly increased (e.g., to above 10 $cmH_2O$), the phase component of the input signal is less influenced by sudden hemodynamic changes compared to the absolute component of the input signal. The present inventors have therefore devised a technique in which the information extracted from the phase component is combined with the information extracted from the absolute component, in a manner such that the phase component provides information indicative of the baseline of the respective quantity, while the absolute component or a combination (e.g., linear combination) of the phase component and the absolute component provides information indicative of variations with respect to the baseline. Thus, information relevant for relatively long time intervals (e.g., of order of tens of minutes to a few hours) is provided by the phase component of the signal, and information relevant for relatively short time intervals (e.g., of order of seconds to several minutes, and more preferably less than one minute) is provided by the absolute component or a combination of the two components of the signal. The combination of these two types of information provides an accurate as well as responsive diagnosis.

Diagnosis pertaining to quantities that vary by an amount of at least 30% within a time window of less than 10 seconds, or less than 5 seconds or less than 2 seconds or less than 1 second is referred to herein as "real-time diagnosis."

In some embodiments of the present invention, the method continues to 24 at which a dynamically adaptive filter is applied. The filter can be applied to the input signal as obtained at 22 or to any of the components obtained at 23. Preferably, the filter is applied at least to the phase component. In some embodiments of the present invention the filter is applied separately to each of the phase and absolute components. The filtration is preferably performed using a digital filter and responsively to the physiological condition of the subject. The filtration can be done, for example, by employing the filtering techniques described in International Patent Publication No. 2009/022330 the contents of which are hereby incorporated by reference, separately to the phase and to the absolute components.

Generally, the dynamically variable filter filters the data according to a frequency band which is dynamically adapted in response to a change in the physiological condition of the subject. It was found by the Inventors of the present invention that the dynamical adaptation of the frequency band to the physiological condition of the subject can significantly reduce the influence of unrelated signals on the measured property.

Thus, in the present embodiment, operation 24 includes a process in which first the physiological condition of the subject is determined, then a frequency band is selected based on the physiological condition of the subject, and thereafter the input signals are filtered according to frequency band. The frequency band is dynamically adapted in response to a change in the physiological condition.

The physiological condition is preferably, but not obligatorily, the heart rate of the subject. The data pertaining to the physiological condition can be collected via a suitable data collection unit either in analog or digital form, as desired. For example, the physiological condition can be a heart rate which can be determined, e.g., by analysis of ECG signals or the like.

While the embodiments below are described with a particular emphasis to physiological condition which is a heart rate, it is to be understood that more detailed reference to the heart rate is not to be interpreted as limiting the scope of the invention in any way. For example, in exemplary embodiments of the present invention the physiological condition is a ventilation rate of the subject, a repetition rate of a particular muscle unit and/or one or more characteristics of an action potential sensed electromyography.

The adaptation of the frequency band to the physiological condition can be according to any adaptation scheme known in the art. For example, one or more parameters of the frequency band (e.g., lower bound, upper bound, bandwidth, central frequency) can be a linear function of a parameter characterizing the physiological condition. Such parameter can be, for example, the number of heart beats per minute.

Figure 3A:
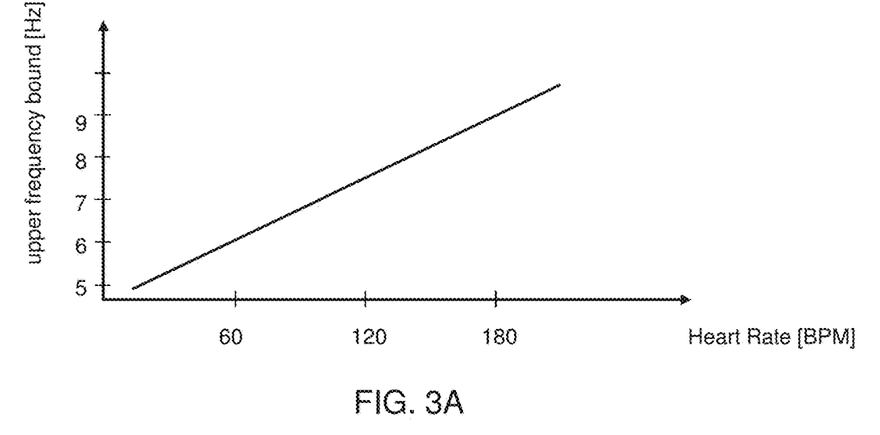
FIGS. 3A-B show a representative example of dynamically varying frequency bounds, employed according to embodiments of the present invention.
Figure 3B:
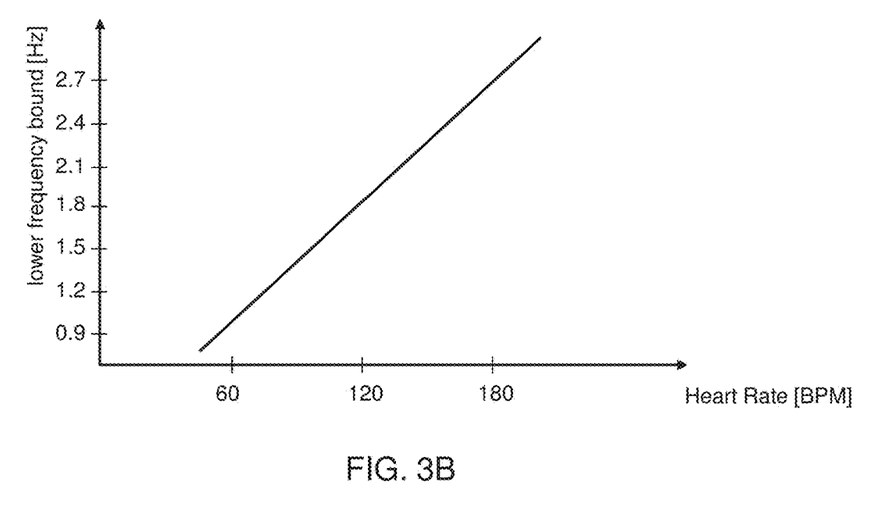

A representative example of a dynamically varying frequency bounds, employed according to some embodiments of the present invention separately to the phase and to the absolute components is illustrated in FIGS. 3A and 3B. Shown in FIGS. 3A and 3B is the functional dependence of the frequency bounds (upper bound in FIG. 3A and lower bound in FIG. 3B) on the heart rate of the subject. As shown in FIG. 3A, the upper bound of the frequency band varies linearly such that at a heart rate of about 60 beats per minute (bpm) the upper bound is about 6 Hz, and at a heart rate of about 180 bpm the upper bound is about 9 Hz. As shown in FIG. 3B, the lower bound of the frequency band varies linearly such that at a heart rate of about 60 the lower bound is about 0.9 Hz bpm and at a heart rate of about 180 bpm the lower bound is about 2.7 Hz.

As used herein the term "about" or "approximately" refers to ±10%.

In some embodiments of the present invention the upper bound approximately equals the function $F_U(HR)$ defined as $F_U(HR)=6+1.5\times[(HR/60)-1]$ Hz, where HR is the heart rate of the subject in units of bpm. In some embodiments, the upper bound equals $F_U(HR)$ at all times, while in other embodiments, the upper bound is set using an iterative process.

In some embodiments of the present invention the lower bound approximately equals the function $F_L(HR)$ defined as $F_L(HR)=0.9\times(HR/60)$ Hz. In some embodiments, the lower bound equals $F_L(HR)$ at all times while in other embodiments the lower bound is set by an iterative process.

Representative examples of iterative process suitable for some embodiments of the present invention are provided hereinunder.

Figure 3C:
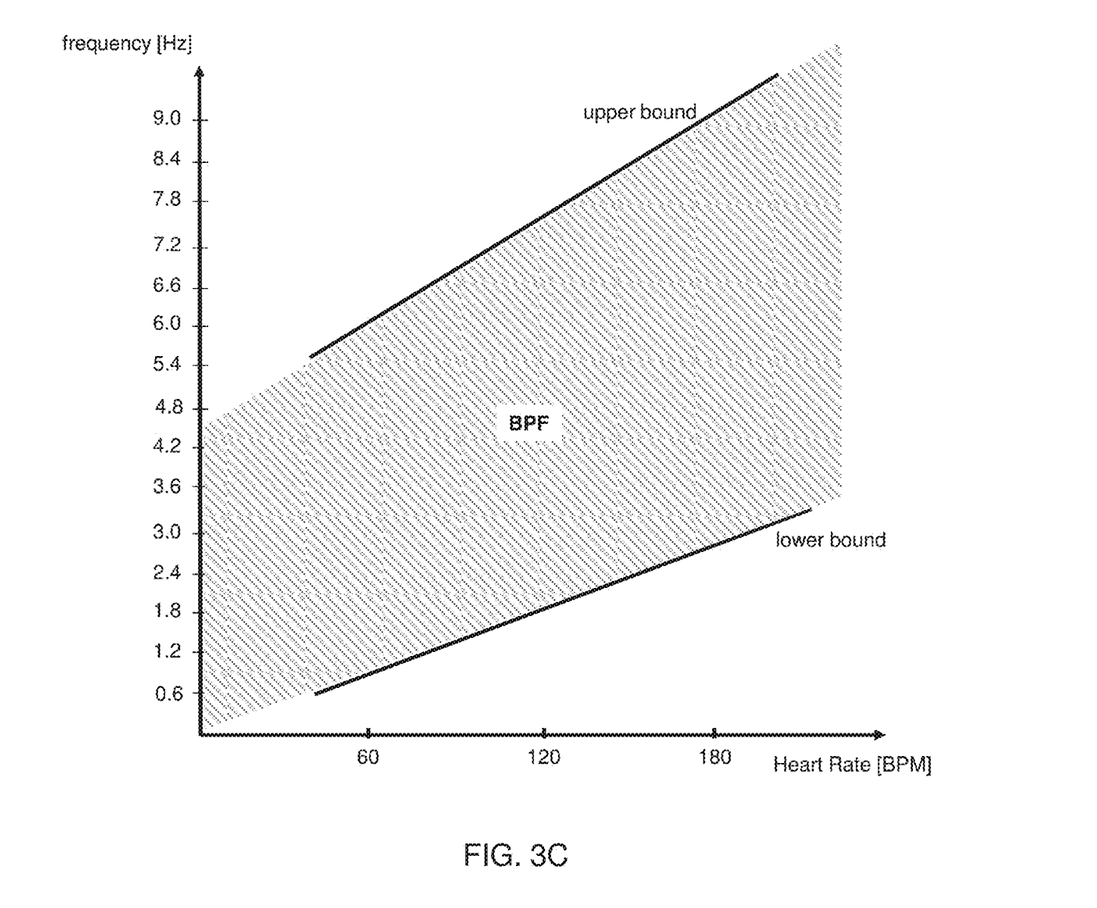
FIG. 3C shows a representative example of a dynamically varying frequency band, employed according to embodiments of the present invention.

A dynamically varying band pass filter (BPF) characterized by a dynamically varying upper frequency bound and a dynamically varying lower frequency bound, according to some embodiments of the present invention is illustrated in FIG. 3C. As shown, each heart rate is associated with a frequency band defined by a lower bound and an upper bound. For example, for a heart rate of 60 bpm, FIG. 3C depicts a BPF in which the lower bound is about 0.9 Hz and the upper bound is about 6 Hz.

It is to be understood that the values presented above and the functional relations illustrated in FIGS. 3A-C are exemplary embodiments and should not be considered as limiting the scope of the present invention in any way. In other exemplary embodiments, the functional relations between the frequency band and the physiological condition can have different slopes and/or offsets, or they can be non-linear.

Following is a description of an iterative process for determining the frequency band of the band pass filter which filters to the phase component and separately the absolute component according to some embodiments of the present invention. The iterative process can, in some embodiments, be based a comparison between a value of a physiological parameter as extracted or calculated from the respective filtered component and a value of the same physiological parameter as extracted or calculated from a reference signal, for example, an ECG signal.

The term "physiological parameter" refers to any variable parameter which is measurable or calculable and is representative of a physiological activity, particularly, but not necessarily, activity of the heart. In various exemplary embodiments of the invention the physiological parameter is other than the heart rate per se. The physiological parameter can be a time-related parameter, amplitude-related parameters or combination thereof.

Typically, the filter signal and the reference signal are expressed in terms of amplitude as a function of the time. Thus, time-related parameters are typically calculated using abscissa values of the signals and amplitude-related parameters are is typically calculated using ordinate values of the signals.

Representative of time-related physiological parameters suitable for the present embodiments include, without limitation, systolic time, diastolic time, pre-ejection period and ejection time. A representative example of amplitude-related physiological parameter suitable for the present embodiments includes, without limitation, maximal amplitude above zero during a single beat, maximal peak-to-peak amplitude during a single beat, and RMS level during a single beat. Also contemplated are various slopes parameters, such as, but not limited to, the average slope between two points over the signal.

In various exemplary embodiments of the invention the physiological parameter is a ventricular ejection time (VET).

While the embodiments below are described with a particular emphasis to VET as the physiological parameter, it is to be understood that more detailed reference to VET is not to be interpreted as limiting the scope of the invention in any way.

The present inventors discovered that a significant amount of the biological information for a particular subject can be obtained from a frequency range between $F_L(HR)$ and 5.5 Hz, where HR is the heart rate of the subject. It was further discovered by the present inventors that for some medical conditions some of the information can reside between 5.5 Hz and $F_U(HR)$.

The advantage of the comparison between two different techniques for extracting or calculating the same physiological parameter, is that it allows to substantially optimize the upper frequency bound of the band pass filter. In various exemplary embodiments of the invention in each iteration of the iterative process, the comparison is repeated. If the comparison meets a predetermined criterion, the upper frequency bound is updated by calculating an average between a low threshold for the upper bound and a high threshold for the upper bound. The lower frequency bound can be a constant bound, e.g., a constant frequency which is from about 0.9 Hz to about 2.7 Hz), or it can be dynamic, e.g., $F_L(HR)$, HR being the heart rate of the subject before or during the respective iteration.

The low and high thresholds for the upper bound can be set in more than one way. In some embodiments, the low and high thresholds are predetermined (namely they determined a priori before the iterative process), in some embodiments, the thresholds are set in a previous iteration of iterative process, in some embodiments one of the thresholds is predetermined and the other threshold is set in a previous iteration of iterative process. In any event, the first iteration is based on two thresholds which are determined a priori before the iterative process. It was found by the inventors of the present invention that, at least initially (i.e., at the first iteration), the first threshold can be about $F_U(40)$, which in various exemplary embodiments of the invention is about 5.5 Hz, and the second threshold can be the calculated value of $F_U(HR)$, HR being the heart rate of the subject before or during the respective iteration.

The predetermined criterion used during the iterations can be, for example, that the results of the two calculations are similar (e.g., within about 40% or 30% or 25% of each other). The predetermined criterion can also relate to the direction of difference between the two calculations. Broadly, for time-related parameters, the upper bound is updated if the value of the parameter as calculated based on the reference signal is higher than value of the parameter as calculated based on the filtered signal, and for amplitude-related parameters the upper bound is updated if the value of parameter as calculated based on the reference signal is lower than the value of the parameter as calculated based on the filtered signal. For slope-related parameters, the upper bound is typically updated if the value of the parameter as calculated based on the reference signal is higher than the value of the parameter as calculated based on the filtered signal.

A Boolean combination between the above criteria can also be used as a criterion. For example, an AND Boolean combination can be employed in which case the upper frequency bound can be updated if the results of the two calculations are similar and the calculation according to the filtered signal indicates an abnormal physiological condition while the calculation according to the reference signal indicates a normal physiological condition.

An iterative process for selecting the upper frequency bound, suitable for some exemplary embodiments of the present invention is described in International Patent Publication No. WO2010/032252, the contents of which are hereby incorporated by reference.

The method can optionally continue to 24 at which blood flow is determined from one or more of the extracted components. In some embodiments of the present invention a baseline blood flow of the subject is determined based on the phase component, and in some embodiments of the present invention transient changes in the blood flow are determined based on the absolute component. The determination of blood flow is preferably performed by a digital processing unit, such as a circuit configured for performing the determination. The method can also employ a digital processing unit, such as, but not limited to, a general purpose computer or dedicated circuitry, to calculate one or more blood flow or blood volume related quantities, such as, but not limited to, stroke volume (SV), cardiac output (CO), ventricular ejection time (VET), cardiac index (CI), thoracic fluid content (TFC), total peripheral resistance index (TPRI), and any combination thereof.

Figure 4:
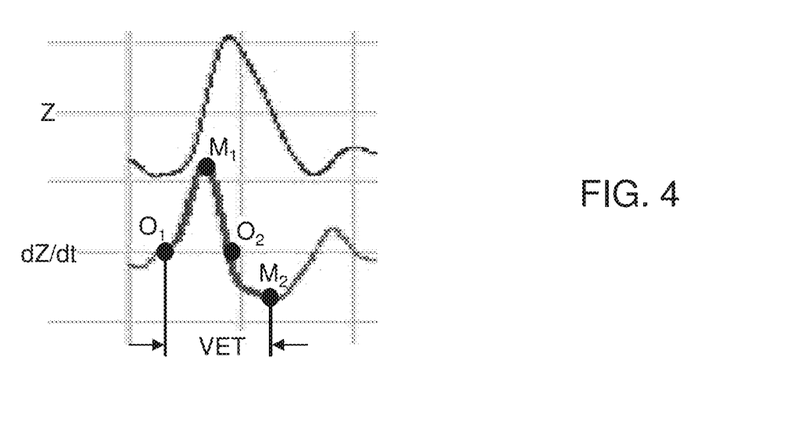
FIG. 4 is a schematic illustration of a procedure for extracting ventricular ejection time from a derivative of a filtered signal according to various exemplary embodiments of the present invention.

For example, the VET can be extracted from the morphology of the pulses of the signal. In some embodiments of the present invention points of transitions are identified on the pulse and the time interval between two such points is defined as the VET. An exemplified procedure is illustrated in FIG. 4, which illustrates a typical morphology of a single beat of the hemodynamic impedance Z and its first derivative dZ/dt, as a function of the time. As shown, dZ/dt has two zeroes $O_1$ and $O_2$ over the beat, with a point of local maximum $M_1$ between the zeroes and a point of local minimum $M_2$ after the second zero. In some embodiments of the present invention the VET is defined as the time period (difference between the abscissa values) between the first zero $O_1$ and the first minimum $M_2$ after the second zero $O_2$.

Other examples include the stroke volume SV and the cardiac output CO. The baseline SV can be calculated using the relation SV=const.×T×Δϕ, where Δϕ is the phase component (e.g., the phase shift of the input signal relative to the output signal), "const." is a constant which can be found, for example, using a calibration curve and T is a time-interval extractable from the signal. In some embodiments of the present invention the time-interval is VET. The cardiac output CO can be calculated using the relation CO=const.× T×Δϕ×HR, where HR is the heart rate of the subject (e.g., in units of beats per minutes), and "const" and T are as further detailed hereinabove.

Additional blood flow or blood volume related quantities can be extracted from the signal or its components as known in the art (see, e.g., International Patent Publication No. WO2010/032252).

The blood flow and blood volume related quantities represent the morphology of the signal. These quantities can therefore be used according to some embodiments of the present invention to calculate the likelihood that the subject develops sepsis.

In various exemplary embodiments of the invention the method continues to 26 at which a sepsis indicator is extracted from the pulse morphology, and to 27 at which the likelihood is assessed based on the sepsis indicator. The assessment can be done, for example, by thresholding, wherein the sepsis indicator as obtained from the pulse morphology is compared to a predetermined threshold which can be used as a criterion to assess whether or not the subject is likely to develop sepsis.

In some embodiments of the present invention the sepsis indicator is a ratio between the time-derivative of the processed signal and the ventricular ejection time.

The processed signal used for calculating the time-derivative and VET can be the impedance or the reactance or any component thereof (e.g., phase component, absolute component), optionally following application of the dynamically variable filter as further detailed hereinabove.

Without wishing to be bound by any particular theory, the present inventors identified that this ratio reflects the relative behavior of contractility per time to eject. Thus, this ratio also reflects the cardiac work against the after load pressures. In cases of hyperdynamic cardiac performance, such as septic shock and liver failure or cirrhosis, the heart contracts in relatively enhanced contractile force against a low after load. This results in a higher value of the ratio. Thus, such a ratio can be used according to some embodiments of the present invention for assessing the likelihood for the subject to develop sepsis. The present inventors conducted experiments and uncovered that this ratio can be used as a discriminator for screening septic and non-septic subjects. It was found that for septic subjects, this ratio is generally high, wherein for non-septic subjects this ratio is generally low.

When the above ratio is used as a sepsis indicator, the ratio is optionally and preferably compared to a predetermined threshold, wherein a ratio above the predetermined threshold indicates that the subject is likely to develop sepsis, and a ratio above the predetermined threshold indicates that the subject is not likely to develop sepsis. Typical values for the predetermined threshold are from about 0.5 to about 0.8, or from about 0.6 to about 0.8, e.g., about 0.7. It was found by the present inventors that using such threshold, the likelihood is characterized by a p-value less than 0.1, e.g., 0.05.

The method can then continue to 28 at which a report is issued. The report can include the assessed likelihood and optionally other parameters, particularly statistical parameters (e.g., characteristic p-value and the like).

The method ends at 29.

Figure 5:
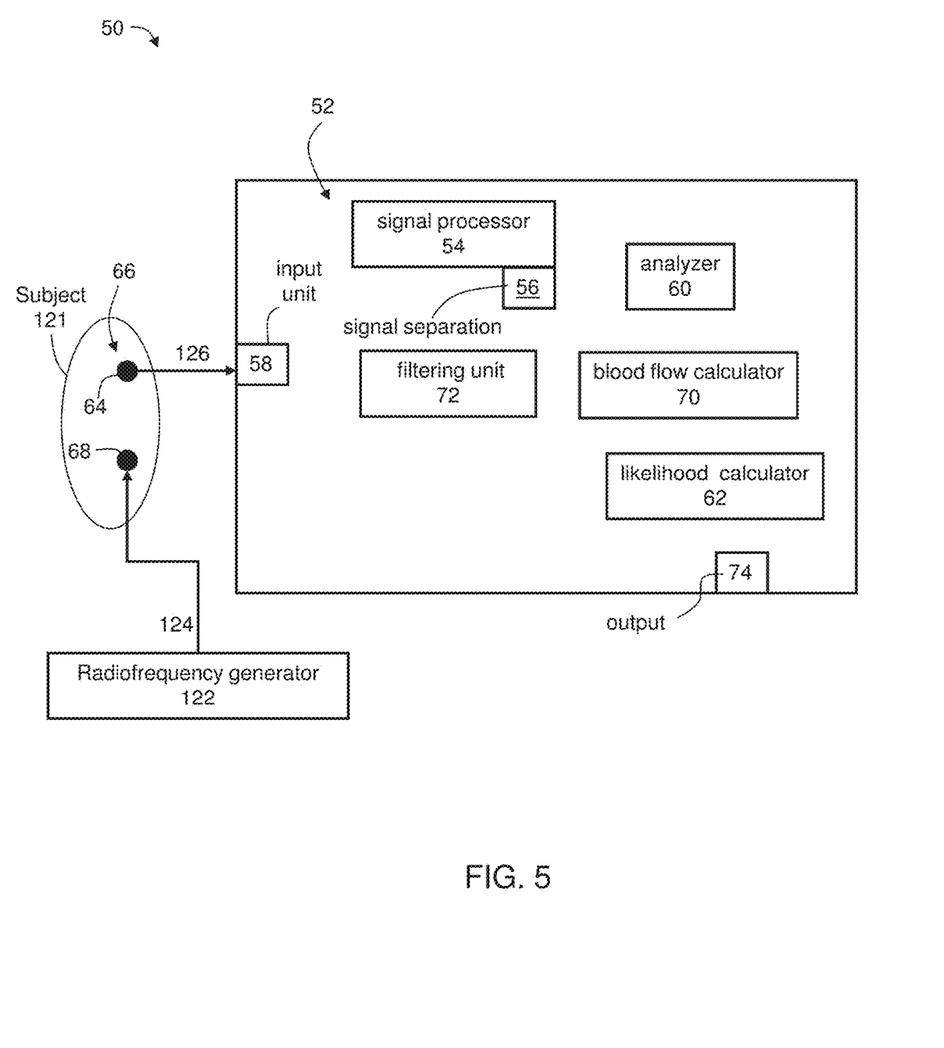
FIG. 5 is a schematic illustration of a system for assessing the likelihood that an infected subject develops sepsis, according to some embodiments of the present invention.

Reference is now made to FIG. 5 which is a schematic illustration of a system 50 for assessing the likelihood that an infected subject develops sepsis; according to some embodiments of the present invention. System 50 comprises an assessment system 52 having a signal processor 54 which receives an input signal, e.g., via an input unit 56, such as an electronic connector optionally associated with a sampler, and processes the signal as further detailed hereinabove. For example, signal processer 54 can extract the impedance from the input signal. In some embodiments of the present invention signal processer 54 comprises a signal separating unit 56 which separates the input signal or the reactance component thereof, to an absolute component and a phase component, as further detailed hereinabove. Signal processor 54 can comprise electronic circuit designed and configured for performing the above operations.

In various exemplary embodiments of the invention system 50 comprises an analyzer 60 configured for analyzing the processed signal received from processor 54 to determine a characteristic pulse morphology of processed signal, and a likelihood calculator 62 which calculates the likelihood that the subject develops sepsis based on characteristic pulse morphology, as further detailed hereinabove.

System 50 can also comprise an input unit 58 for receiving the input signals sensed from the organ. The input signals typically comprise radiofrequency signals related to the electrical properties of the organ (e.g., bioimpedance which may generally relate to the impedance and/or hemodynamic reactance of the organ). The signals are sensed via a plurality of electrodes 64 at one or more sensing locations 66 on the organ of subject 121 and are originated by output signals 124 generated by a radiofrequency generator 122, and transmitted to the organ by one or more electrodes 68.

In some embodiments of the present invention system 50 comprises a blood flow calculator 70 which calculates the blood flow using processed signal, wherein the likelihood calculator 62 is configured to calculate likelihood based, at least in part, on the calculated blood flow, as further detailed hereinabove.

In some embodiments of the present invention system 50 comprises a filtering unit 72 which filters the processed input signals. Unit 72 preferably performs the filtration operation in the frequency domain. Thus, in various exemplary embodiments of the invention, a series of samples of the processed radiofrequency signals are transformed, e.g., by a Fast Fourier Transform (FFT), to provide a spectral decomposition of the signals in the frequency domain. The transformation to the frequency domain can be done by a data processor. Algorithms for performing such transformations are known to those skilled in the art of signal processing.

The obtained spectral decomposition of the signal is filtered by unit 72 which typically eliminates one or more of the frequencies in the spectrum, depending on the upper and lower frequency bounds of the filter employed by unit 72. Unit 72 preferably employs a dynamically variable filter, such as, but not limited to, the dynamically variable filer described hereinabove.

In various exemplary embodiments of the invention system 50 comprises an output unit 74 which provides indication regarding the estimated likelihood. Output unit 74 can be embodied as a display device which displays the estimated likelihood. Unit 74 can also comprise a communication device which transmits the estimated likelihood to another system located nearby or at a remote location. The communication can be wireless or wired, as desired.

Following are technical preferred values which may be used for selective steps and parts of the embodiments described above.

The output signals are typically from about 10 KHz to about 200 KHz in frequency and from about 10 mV to about 200 mV in magnitude; the input signals are typically about 75 KHz in frequency and about 20 mV in magnitude; a typical impedance which can be measured by the present embodiments is from about 5 Ohms to about 75 Ohms; the resulting signal-to-noise ratio of the present embodiments is at least 40 dB; and the signal are typically sampled at a rate of about 500-1000 samples per second.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Experiments have been performed to investigate the ability of the present embodiments to assess the likelihood that subjects develop sepsis.

The experiments included analysis of data acquired from 68 patients, all ages above 18 years. The initial classification of all patients, as made professional practitioners at enrollment time, was suspected infection (29 patients) or suspected sepsis (39 patients).

Each subject underwent conventional diagnosis by professional medical practitioners at the hospital. Of the 68 patients, 23 were diagnosed as having sepsis, 2 were diagnosed as having septic shock, 14 were diagnosed as having infection, 16 were diagnosed as having a systemic inflammatory response syndrome (SIRS) without infection, and 13 were diagnosed as not having infection.

The patients also underwent likelihood assessment according to some embodiments of the present invention. A hemodynamic impedance signal was acquired from each patient using four dual surface electrodes connected to four corners of the thoracic body surface of the patient.

The patients were asked to sit without or with minimal motion for about 3 minutes, during which measurements of hemodynamic impedance were recorded. Thereafter, the patients were asked to lie on the bed in supine position for about 3 additional minutes during which additional measurements of hemodynamic impedance were recorded. The recordings were paused during the transition of the patients from the sitting position to the supine position.

The phase component was extracted from the hemodynamic impedance. The time-derivative of the phase component was used for estimating the VET of each patient, as explained above with reference to FIG. 4. The ratio between the time-derivative of the phase component and the estimated VET was used as a sepsis indicator. The likelihood was assessed by comparing the sepsis indicator to a predetermined threshold, wherein patients with sepsis indicator above the threshold were identified is likely to have sepsis.

Figure 6:
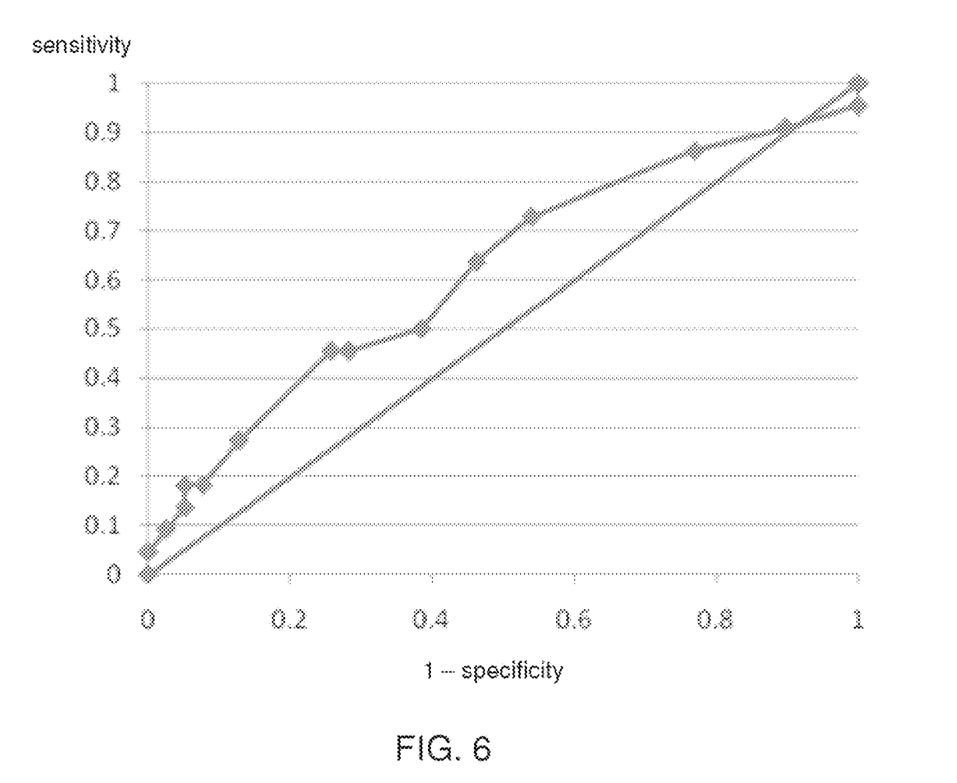
FIG. 6 is a receiver operating characteristic (ROC) curve, obtained in experiments performed according to some embodiments of the present invention.

Table 1 below summarizes the Statistical Sensitivity (Sn) and Specificity (Sp) for different values of the threshold. The corresponding receiver operating characteristic (ROC) curve (Sn vs. 1-Sp) is shown in FIG. 6. The straight line in FIG. 6 is the random guess line, and the curved line corresponds to the data in Table 1.

TABLE 1

| Threshold | Sensitivity | Specificity |
|---|---|---|
| 0 | 1 | 0 |
| 0.1 | 1 | 0 |
| 0.2 | 1 | 0 |
| 0.3 | 0.95 | 0 |
| 0.4 | 0.91 | 0.10 |
| 0.5 | 0.86 | 0.23 |
| 0.6 | 0.73 | 0.46 |
| 0.7 | 0.64 | 0.54 |
| 0.8 | 0.5 | 0.62 |
| 0.9 | 0.45 | 0.72 |
| 1 | 0.45 | 0.74 |
| 1.25 | 0.27 | 0.87 |
| 1.5 | 0.18 | 0.92 |
| 1.75 | 0.18 | 0.95 |
| 2 | 0.14 | 0.95 |
| 2.5 | 0.09 | 0.97 |
| 3 | 0.05 | 1 |

Table 1 and FIG. 6 demonstrate that the ratio between the time-derivative of the phase component and the estimated VET can be used as sepsis indicator. In some embodiments of the present invention the threshold is set to about 0.7, corresponding to sensitivity of about 64% and specificity of about 54%. In some embodiments, the threshold is set to 0.6 corresponding to sensitivity of about 72% and specificity of about 46%. It is envisioned that due to the high mortality rate of sepsis, it will be desired to prefer high sensitivity values to high specificity values.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of assessing the likelihood that an infected subject develops sepsis, the method comprising:
    transmitting, by a plurality of electrodes, an output radiofrequency signal to the subject;
    receiving, by an input unit, an input radiofrequency signal received from the subject responsively to transmitting said output radiofrequency signal;
    processing, by a signal processor, said input radiofrequency signal to provide a processed signal;
    storing said processed signal in a memory;
    using said processed signal for calculating a ventricular ejection time;
    extracting a time-derivative of said processed signal;
    storing said ventricular ejection time and said time-derivative in said memory;
    analyzing, using an analyzer, said processed signal to determine a characteristic pulse morphology of said processed signal by calculating a ratio between said time-derivative and said ventricular ejection time;
    using said characteristic pulse morphology for assessing, using a likelihood calculator, the likelihood that the subject develops sepsis; and
    displaying said likelihood on a display.

2. The method according to claim 1, further comprising using said processed signal for calculating a blood flow quantity, wherein said likelihood is assessed based, at least in part, on said blood flow quantity.

3. The method according to claim 1, wherein said assessing said likelihood comprises comparing said ratio to a predetermined threshold, and wherein a ratio above said predetermined threshold indicates that the subject is likely to develop sepsis.

4. The method according to claim 3, wherein said threshold is from about 0.5 to about 0.8, and wherein said likelihood is characterized by a p-value less than 0.1.

5. The method according to claim 1, wherein said processing comprises acquiring an absolute component and a phase component of said input signal, and wherein said analyzing said processed signal comprises separately analyzing at least one of said phase component and said absolute component.

6. The method according to claim 5, further comprising identifying disturbances in said input signal based on said absolute component, and correcting said characteristic pulse morphology according to said identified disturbances.

7. The method according to claim 5, further comprising identifying body movements of the subject based on said absolute component.

8. The method according to claim 5, further comprising identifying muscle activity of the subject based on said absolute component.

9. A system for assessing the likelihood that an infected subject develops sepsis, the system comprising:
- a plurality of electrodes configured for transmitting said output radiofrequency signal to the subject;
- an input unit configured for receiving an input radiofrequency signal received from the subject responsively to said output radiofrequency signal;
- a signal processor including a memory, said signal processor configured for processing said input radiofrequency signal to provide a processed signal and storing said processed signal in said memory;
- an analyzer configured for analyzing said processed signal to calculate a ventricular ejection time using said processed signal, for extracting a time-derivative of said processed signal, for storing said ventricular ejection time and said time-derivative in said memory, and for determining a characteristic pulse morphology of said processed signal by calculating a ratio between said time-derivative and said ventricular ejection time;
- a likelihood calculator configured for calculating the likelihood that the subject develops sepsis based on said characteristic pulse morphology; and
- a display for displaying said likelihood.

10. The system according to claim 9, further comprising:
- a radiofrequency generator for generating said output radiofrequency signal; and
- wherein said plurality of electrodes configured for sensing an input radiofrequency signal from the subject.

11. The system according to claim 9, further comprising a blood flow calculator configured for calculating blood flow using said processed signal, wherein said likelihood calculator is configured to calculate said likelihood based, at least in part, on said blood flow.

12. The system according to claim 9, wherein said analyzer is configured for extracting a time-derivative of said processed signal.

13. The system according to claim 9, wherein said likelihood calculator is configured to compare said ratio to a predetermined threshold, and wherein a ratio above said predetermined threshold indicates that the subject is likely to develop sepsis.

14. The system according to claim 13, wherein said threshold is from about 0.5 to about 0.8, and wherein said likelihood is characterized by a p-value less than 0.1.

15. The system according to claim 9, wherein said signal processor comprises a signal separating unit configured for separating said input signal to an absolute component and a phase component, and wherein said analyzer is configured for separately analyzing at least one of said phase component and said absolute component.

16. The system according to claim 15, wherein said analyzer is configured for identifying disturbances in said input signal based on said absolute component, and correcting said characteristic pulse morphology according to said identified disturbances.

17. The system according to claim 15, wherein said analyzer is configured for identifying body movements of the subject based on said absolute component.

18. The system according to claim 15, wherein said analyzer is configured for identifying muscle activity of the subject based on said absolute component.

19. A method of assessing the likelihood that an infected subject develops sepsis, the method comprising:
- transmitting, by a plurality of electrodes, an output radiofrequency signal to the subject;
- receiving, by an input unit, an input radiofrequency signal from the subject responsively to transmitting said output radiofrequency signal;
- acquiring, by a signal processor, an absolute component and a phase component of said input radiofrequency signal;
- storing said components in a memory;
- analyzing, using an analyzer, at least one of said phase component and said absolute component to determine a characteristic pulse morphology of said at least one component and storing said pulse morphology in a memory;
- using said characteristic pulse morphology for assessing, using a likelihood calculator, the likelihood that the subject develops sepsis; and
- displaying said likelihood on a display.

20. A system for assessing the likelihood that an infected subject develops sepsis, the system comprising:
- a plurality of electrodes configured for transmitting said output radiofrequency signal to the subject;
- an input unit configured for receiving an input radiofrequency signal received from the subject responsively to said output radiofrequency signal;
- a signal processor including a memory, said signal processor configured for acquiring an absolute component and a phase component of said input radiofrequency signal, and storing said components in said memory;
- an analyzer configured for analyzing at least one of said phase component and said absolute component to determine a characteristic pulse morphology of at least one of said phase component and said absolute component;
- a likelihood calculator configured for calculating the likelihood that the subject develops sepsis based on said characteristic pulse morphology; and
- a display for displaying said likelihood.

* * * * *